(12) United States Patent
Nakata et al.

(10) Patent No.: US 8,498,445 B2
(45) Date of Patent: Jul. 30, 2013

(54) MATERIAL DETERMINING APPARATUS FOR STEEL PRODUCT AND MATERIAL DETERMINING METHOD FOR STEEL PRODUCT

(75) Inventors: Takeo Nakata, Osaka (JP); Masami Ikeda, Osaka (JP); Kenji Fujiwara, Amagasaki (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 231 days.

(21) Appl. No.: 13/002,531

(22) PCT Filed: Jul. 6, 2009

(86) PCT No.: PCT/JP2009/062271
§ 371 (c)(1),
(2), (4) Date: Feb. 9, 2011

(87) PCT Pub. No.: WO2010/004947
PCT Pub. Date: Jan. 14, 2010

(65) Prior Publication Data
US 2011/0158471 A1 Jun. 30, 2011

(30) Foreign Application Priority Data
Jul. 8, 2008 (JP) ................................. 2008-177650

(51) Int. Cl.
G06K 9/00 (2006.01)
G06K 9/46 (2006.01)
G06K 9/66 (2006.01)

(52) U.S. Cl.
USPC ............ 382/103; 382/100; 382/141; 382/194

(58) Field of Classification Search
None
See application file for complete search history.

(56) References Cited

U.S. PATENT DOCUMENTS
2003/0228066 A1  12/2003  Tomita et al.

FOREIGN PATENT DOCUMENTS
JP  06-123706  5/1994
JP  07-294438  11/1995
(Continued)

OTHER PUBLICATIONS
JIS G 0566: 1980 (English version).*
(Continued)

*Primary Examiner* — Matthew Bella
*Assistant Examiner* — Thomas Conway
(74) *Attorney, Agent, or Firm* — Clark & Brody

(57) ABSTRACT

An object of the invention is to provide a material determining apparatus for a steel product and a material determining method for a steel product which can stably and precisely determine a carbon content of the steel product. The invention provides a material determining apparatus for a steel product, which is provided with an imaging device for continuously imaging a spark generated during rubbing the steel product at a plurality of times, a detecting part for detecting spark regions and bursting spark regions from each of the imaged pictures imaged by the imaging device, a calculating part for calculating a total of the spark regions and a total of the bursting spark regions by summing up the numbers of the spark regions and the bursting spark regions detected by the detecting part with regard to each of all the imaged pictures, so as to calculate a rate of the total of the bursting spark regions with respect to the total of the spark regions, and a determining part for determining a carbon content of the steel product based on the rate, and a material determining method for the steel product.

6 Claims, 9 Drawing Sheets

FOREIGN PATENT DOCUMENTS

| JP | 07294437 A | * 11/1995 |
| --- | --- | --- |
| JP | 08-86730 | 4/1996 |
| JP | 2000-2523 | 1/2000 |
| JP | 3482265 | 12/2003 |
| JP | 2004-69673 | 3/2004 |

OTHER PUBLICATIONS

Masaaki et al., JP 07-294438 A (machine translation).*

Yonezawa et al., Discrimination of Steel Types by Sparks: Applying Neural Network, Fuzzy Systems, 1995. International Joint Conference of the Fourth IEEE International Conference on Fuzzy Systems and The Second International Fuzzy Engineering Symposium., Proceedings of 1995 IEEE Int, vol. 1, pp. 415-420.*

Bermann, Testing Steel by Sparks, The Literay Digest, Nov. 20, 1909, pp. 902.*

Buzzard, The Utility of the Spark Test as Applied to Commercial Steels, Part of Bureau of Standards Journal of Research, vol. 11, Oct. 1933, pp. 527-540.*

Nippon Kogyo Kikaku Hagane no Hibana Shiken Hoho, JIS G 0566, Japanese Standards Association, 1980.

* cited by examiner

MATERIAL DETERMINING APPARATUS FOR STEEL PRODUCT AND MATERIAL DETERMINING METHOD FOR STEEL PRODUCT

BACKGROUND OF THE INVENTION

1. Field of the Invention

The present invention relates to a material determining apparatus for a steel product and a material determining method for a steel product which determine a material of the steel product.

2. Description of the Related Art

As a method of determining a carbon content of a steel product, there has been known a method of taking a view of a state of a spark generated during rubbing the steel product by means of a grinder or the like by an examining staff in accordance with a visual observation and determining the carbon content of the steel product based on the state of the spark by the examining staff. However, in the method mentioned above, since a result of determination depends on an individual skill of the examining staff, there are problems that the result of determination becomes inaccurate, and a skilled examining staff is necessary.

A steel product examining apparatus for the purpose of solving the above problems is disclosed in Japanese Patent No. 3482265 (Patent Document 1). The steel product examining apparatus disclosed in Patent Document 1 images a spark generated during rubbing the steel product by a grinder or the like. Further, the steel product examining apparatus sets a circular region around a position of a gravity point of a bursting spark region corresponding to each of the bursting sparks in an imaged picture to the imaged picture. Further, the steel product examining apparatus determines a carbon content of the steel product based on an area of the bursting spark region occupied in each of the circular regions, and the number of intersections at which an outer peripheral edge of each of the circular regions intersects the bursting spark region.

SUMMARY OF THE INVENTION

However, the area of the bursting spark region occupied in the circular region, and the number of the intersections at which the outer peripheral edge of the circular region intersects the bursting spark region depend on the number and the magnitude of the bursting spark, and the like. The number and the magnitude of the bursting spark depends on a pressing force of the grinder or the like applied to the steel product, and a contact area between the steel product and the grinder or the like, in addition to the carbon content of the steel product. Accordingly, the area of the bursting spark region occupied in the circular region, and the number of the intersections at which the outer peripheral edge of the circular region intersects the bursting spark region are changed depending on the pressing force of the grinder or the like applied to the steel product, and the contact area between the steel product and the grinder or the like. Therefore, the steel product examining apparatus disclosed in Patent Document 1 has a case that it cannot accurately determine the carbon content of the steel product.

An object of the present invention is therefore to provide a material determining apparatus for a steel product and a material determining method for a steel product which can stably and precisely determine a carbon content of the steel product.

The present invention provides a material determining apparatus for a steel product comprising: an imaging device for continuously imaging a spark generated during rubbing the steel product at a plurality of times; a detecting part for detecting spark regions and bursting spark regions having three or more end portions among the spark regions, from each of the imaged pictures imaged by the imaging device; a calculating part for calculating a total of the spark regions and a total of the bursting spark regions by summing up the numbers of the spark regions and the bursting spark regions detected by the detecting part with regard to each of all the imaged pictures, so as to calculate a rate of the total of the bursting spark regions with respect to the total of the spark regions; and a determining part for determining a carbon content of the steel product based on the rate.

The spark generated during rubbing the steel product includes a bursting spark which bursts, and a streamline spark which does not burst. Since a branch is generated by bursting in the bursting spark, it has three or more end portions, and since the streamline spark does not burst, it has two end portions. A rate (hereinafter, refer to as a "actual bursting rate") of the number of the bursting spark with respect to the number of the sparks (that is, (the number of the bursting sparks)+(the number of the streamline sparks)) generated during rubbing the steel product depends on the carbon content of the steel product. On the other hand, the actual bursting rate does not depend on a pressing force of the grinder or the like applied to the steel product, and a contact area between the steel product and the grinder or the like. The material determining apparatus for the steel product in accordance with the present invention determines the carbon content of the steel product based on a rate (hereinafter, refer appropriately to as a "bursting rate") of a total of the bursting spark regions with respect to a total of the spark regions. Accordingly, the result of determination is not affected by the pressing force of the grinder or the like applied to the steel product, and the contact area between the steel product and the grinder. Therefore, the material determining apparatus for the steel product in accordance with the present invention can stably and precisely determine the carbon content of the steel product.

A gray level of the spark region in the imaged picture imaged by an imaging device is different between a center portion and a peripheral portion even within the same spark region, and is different between the spark regions. Accordingly, in the case of detecting the spark region and the bursting spark region based on the imaged picture in accordance with a binarization of the imaged picture, it is hard to detect all the pixels constructing the spark region if a threshold value used for binarizing is large, so that it is hard to accurately detect the spark region and the bursting spark region. On the other hand, if the threshold value used for binarizing is small, the gray level in the peripheral region of the spark region having a comparatively large gray level becomes equal to or more than the threshold value, it is hard to accurately detect the spark region and the bursting spark region.

From the point of view of detecting accurately the spark region and the bursting spark region, preferably, the detecting part carries out the following steps: a first detecting step of detecting a spark candidate pixel group constructed by pixels which are continuous along one pixel line among pixel lines constructing each of the imaged pictures imaged by the imaging device, and which have gray levels that are equal to or more than a first threshold value; a second detecting step of detecting a maximum gray level among the gray levels of the pixels constructing the spark candidate pixel group, and binarizing the pixels constructing the spark candidate pixel group by a second threshold value which is less than the maximum gray level and is more than the first threshold value, and which has a predetermined rate with respect to the maximum gray level, thereby detecting the pixels constructing a spark pixel group from the pixels constructing the spark candidate pixel group; and an identifying step of preparing a binarized image expressing the spark pixel group for each of the imaged pictures by executing the first detecting step and the second detecting step with respect to all the pixel lines constructing each of the imaged pictures, and identifying the spark pixel groups which are continuous with any direction in the each of the binarized images as the spark region.

The region which is away from the spark region is not affected by the spark at all, or is hardly affected by the spark. Accordingly, the gray level is very small in the region which is away from the spark region in comparison with the spark region. If the first threshold value used in the first detecting step is set to a value which is more than the gray levels of the pixels constructing the region which is away from the spark region, it is possible to exclude the pixel constructing the region which is away from the spark region from the pixel which is detected as a spark candidate pixel group. On the other hand, in the preferable structure, the pixel having the gray level which is equal to or more than the first threshold value, and succeeding along the pixel line is detected as one spark candidate pixel group. Accordingly, if the first threshold value is set to a value which is equal to or less than a gray level (hereinafter, refer, appropriately, to as a minimum gray level) of the pixel having the smallest gray level in the pixels constructing the spark region, all the pixels constructing the spark region constructed by the pixels which succeed along the pixel line are detected as one spark candidate pixel group. In this case, if the first threshold value is set to a value which is equal to or less than the minimum gray level, there is a possibility that the gray levels of the pixels constructing the peripheral region of the spark region becomes equal to or more than the first threshold value. If the gray levels of the pixels constructing the peripheral region is equal to or more than the first threshold value, the pixels having the gray levels which is equal to or more than the first threshold value succeed over the spark region and the peripheral region thereof. In this case, the pixels constructing one spark region and the pixels constructing the peripheral region thereof are detected as one spark candidate pixel group. In the structure mentioned above, the second detecting step is carried out per the spark candidate pixel group, and the second threshold value used in the second detecting step is less than the maximum gray level of the pixel constructing the spark candidate pixel group, and has a predetermined rate with respect to the maximum gray level. In the spark region and the peripheral region thereof, the gray level is larger in the spark region. Accordingly, in the case that the spark candidate pixel group is constructed by the pixels constructing one spark region and the pixels constructing the peripheral region thereof, it is possible to make the gray levels of the pixels constructing the peripheral region less than the second threshold value, by suitably setting the predetermined rate mentioned above. Therefore, in accordance with the preferable structure, it is possible to precisely detect the spark pixel group constructing the pixels constructing the spark region. The spark pixel groups succeeding in a predetermined direction is identified as the spark region. Therefore, in accordance with the preferable structure, it is possible to accurately detect the spark region and the bursting spark region.

Preferably, the detecting part applies a thinning process to the binarized images, identifies the spark pixel groups which are continuous with any direction in the each of the binarized images applied to the thinning process as the spark region, and, identifies the spark region as the bursting spark region if the spark region has three or more end portions.

In accordance with the preferable structure, identifying the spark region having three or more end portions as the bursting spark region is carried out after applying the thinning process. Since the identification of the end portion can be easily carried out after applying the thinning process, it is possible to easily identify the bursting spark region in accordance with the preferable structure.

Preferably, the steel product consists of carbon steel or alloy steel, and wherein the determining part determines that the steel product consists of alloy steel in the case that the total of the spark regions is less than a third threshold value, determines that the steel product consists of carbon steel in the case that it is equal to or more than the third threshold value, and determines the carbon content of the steel product based on the rate in the case of determining that the steel product consists of the carbon steel.

The number of the sparks generated during rubbing the steel product consisting of alloy steel is significantly small in comparison with the number of the sparks generated during rubbing the steel product consisting of carbon steel. Therefore, in accordance with the preferable structure, it is possible to determine whether the steel product consists of carbon steel or alloy steel.

Further, the present invention provides a material determining method for a steel product comprising: an imaging step of continuously imaging a spark generated during rubbing the steel product at a plurality of times; a detecting step of detecting spark regions and bursting spark regions having three or more end portions among the spark regions, from each of the imaged pictures imaged in the imaging step; a calculating step of calculating a total of the spark regions and a total of the bursting spark regions by summing up the numbers of the spark regions and the bursting spark regions detected in the detecting step with regard to each of all the imaged pictures, so as to calculate a rate of the total of the bursting spark regions with respect to the total of the spark regions; and a determining step of determining a carbon content of the steel product based on the rate.

Preferably, the imaging step images the spark generated by rubbing the steel product by the rubbing member, in a state in which the rubbing member is pressed to the steel product by a force which is equal to or more than 2.94 N and equal to or less than 9.8 N.

If the pressing force of the rubbing member such as the grinder or the like applied to the steel product is made equal to or more than 2.94 N, the number of the sparks generated during rubbing the steel product by the rubbing member is large, and it is possible to make a difference between the bursting rate and the actual bursting rate small. Therefore, in accordance with the preferable structure, it is possible to precisely and stably determine the carbon content of the steel product. Further, if the pressing force of the rubbing member applied to the steel product is set to 9.8 N or less, it is possible to determine the carbon content of the steel product without applying any deep scratch to the steel product.

In the above description, there is explained the matter the carbon content of the steel product is determined based on the bursting rate. However, the alloy component constructed by the elements such as Cr, Mo, Ti, Mn and the like in addition to the carbon component is included in the component constructing the material of the steel product. Accordingly, in the case that the material of the steel product is precisely determined, the alloy component content of the steel product is an important element in addition to the carbon content of the steel product. As mentioned above, the carbon content of the steel product can be precisely determined based on the bursting rate. However, since the change of the bursting rate is small in comparison with the alloy component content of the steel product, the alloy component content of the steel product cannot be precisely determined based on the bursting rate.

Preferably, the determining part determines the material of the steel product based on the carbon content determined based on the rate, and an alloy component content of the steel product determined by a method which does not utilize a spark generated during rubbing the steel product.

In accordance with the method which does not utilize the spark generated during rubbing the steel product, it is possible to precisely determine the alloy component content of the steel product, in comparison with the case of determining the alloy component content of the steel product based on the rate (the bursting rate). Therefore, in accordance with the preferable structure, it is possible to more precisely determine the material of the steel product. In this case, as the method which does not utilize the spark generated during rubbing the steel product, there can be listed up a fluorescent X-ray analyzing method. Further, in the case that the alloy component of the steel product is constructed by the components of plural kinds of elements, the alloy component content of the steel product means the content of the component of each of the elements constructing the alloy component of the steel product.

The present invention can provide a material determining apparatus for a steel product and a material determining method for a steel product which can stably and precisely determine a carbon content of the steel product.

DESCRIPTION OF THE PREFERRED EMBODIMENTS

Figure 1:
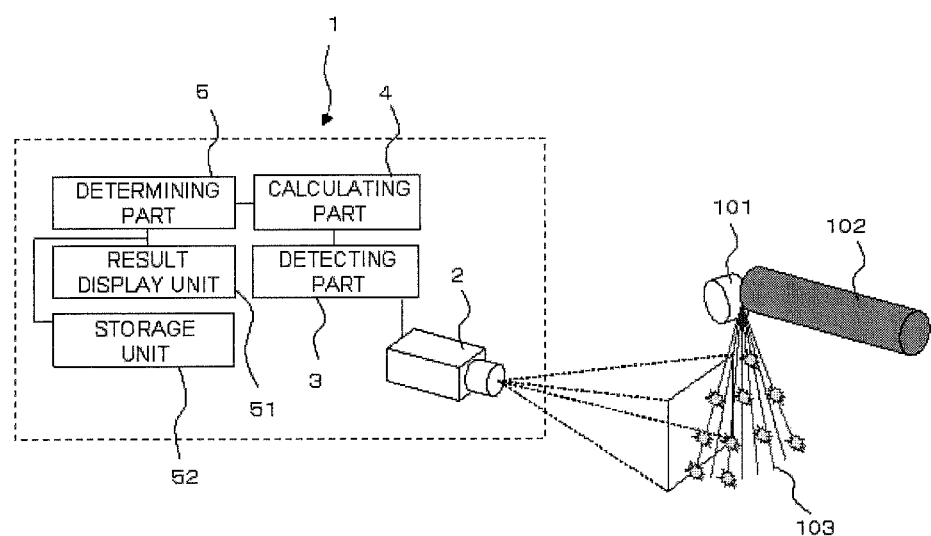
FIG. 1 is a schematic view of a material determining apparatus of a steel product.

FIG. 1 is a schematic view of a material determining apparatus 1 of a steel product (hereinafter, refer to as a "material determining apparatus 1") in accordance with the present embodiment. As shown in FIG. 1, the material determining apparatus 1 in accordance with the present embodiment determines a carbon content included in a steel product 102 based on a spark 103 generated during pressing a rubbing member such as a grinder 101 to the steel product 102 so as to rub. The material determining apparatus 1 is provided with an imaging device 2, a detecting part 3, a calculating part 4, and a determining part 5.

Figure 2:
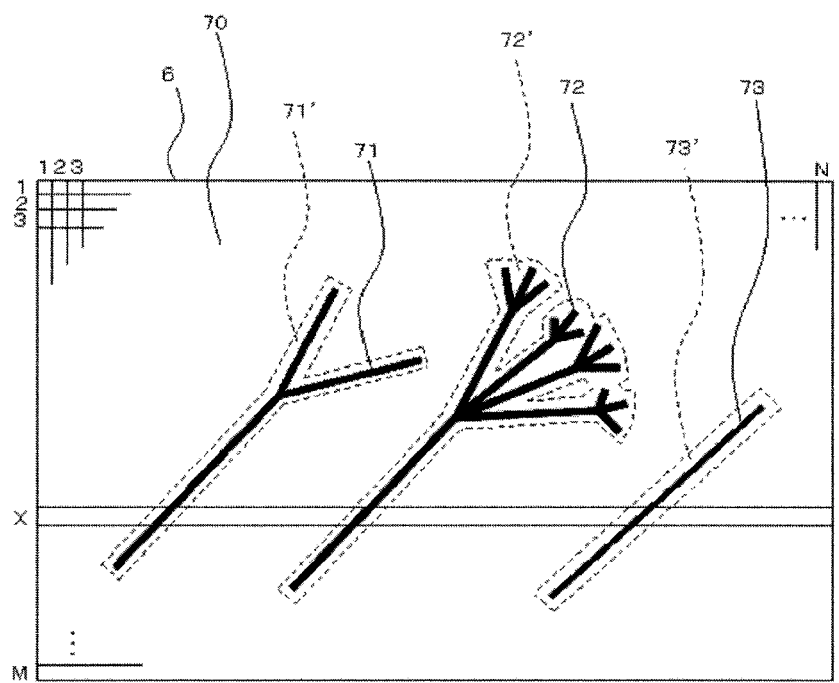
FIG. 2 is a schematic view of an imaged picture which a imaging device images.
Figure 3:
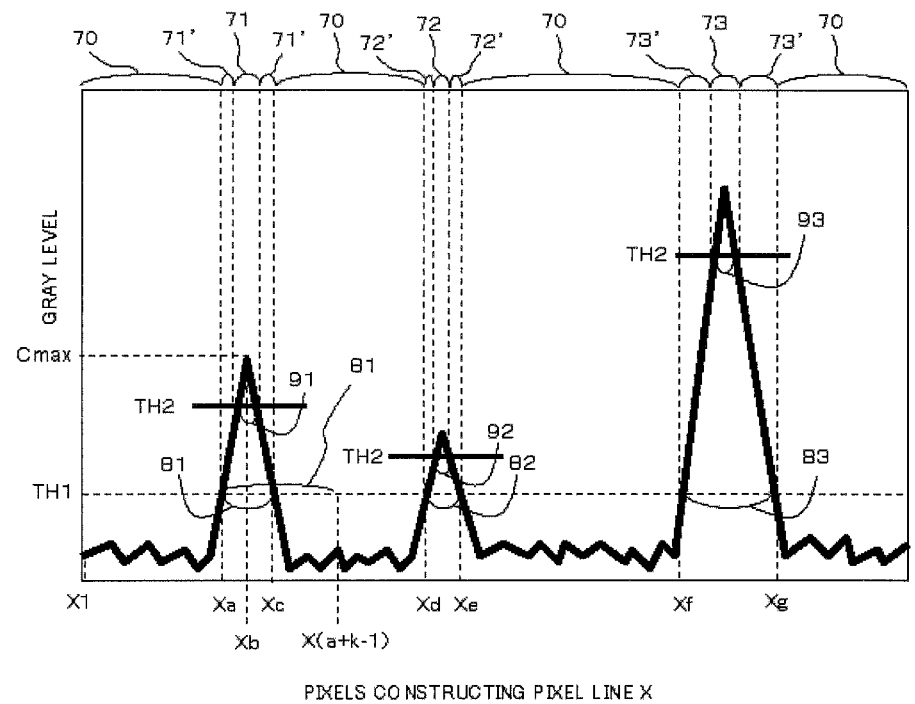
FIG. 3 is a graph showing a gray level of each of a pixels constructing a pixel line X shown in FIG. 2.

The imaging device 2 images the spark 103 generated during rubbing the steel product 102 at a plurality of times continuously. FIG. 2 is a schematic view of an imaged picture 6 which the imaging device 2 images. As shown in FIG. 2, the imaged picture 6 is constructed by M×N number of pixels which are arranged as a matrix shape, and has M number of pixel lines. The imaged picture 6 has spark regions 71 to 73, peripheral regions 71' to 73' of the respective spark regions 71 to 73, and the other region 70 (a region which is away from the spark regions 71 to 73). FIG. 3 is a graph showing a gray level of each of the pixels constructing a pixel line X shown in FIG. 2. As shown in FIG. 3, the gray level is larger in each of the spark regions 71 to 73 than each of the peripheral regions 71' to 73' of the spark regions 71 to 73, and the gray level is larger in each of the peripheral regions 71' to 73' than the other region 70. In this case, since a brightness of the peripheral portion is smaller in comparison with a brightness of the center portion, in the spark, the gray level of the peripheral portion is smaller in comparison with the gray level of the center portion, in the spark region. Further, since the brightness between the sparks 103 is not uniform, the gray level is different between the spark regions 71 to 73. In this case, the spark region has a bursting spark region and a streamline spark region. The bursting spark region is a spark region having three or more end portions. Accordingly, the spark region 71 and the spark region 72 shown in FIG. 2 are the bursting spark region. In this case, the spark region 71 has three end portions, and the spark region 72 has thirteen end portions. Further, the streamline spark region is a spark region having two end portions. Accordingly, the spark region 73 shown in FIG. 2 is the streamline spark region 73.

Figure 4:
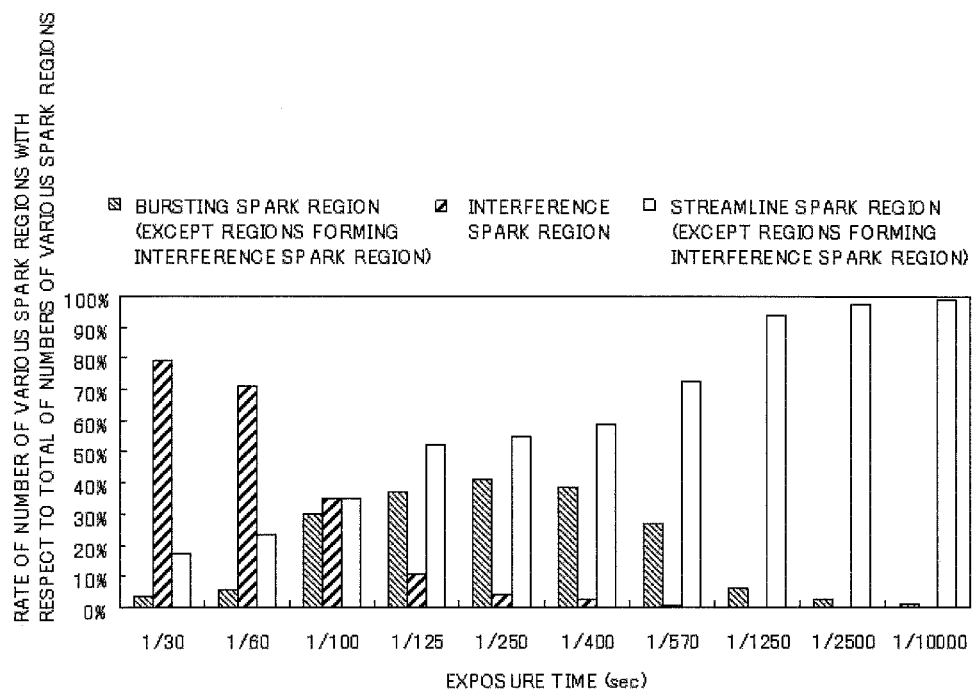
FIG. 4 is a graph showing an exposure time of the imaging device, and a rate of a numbers of a various spark regions with respect to a total of numbers of the various spark regions appearing in the imaged picture, in the case that a peripheral speed of the grind stone of a grinder is 30 mm/sec.

An exposure time of the imaging device 2 is made shorter in accordance with a peripheral speed of a grind stone of the grinder 101 becomes higher. The exposure time of the imaging device 2 is set as mentioned above because of the following reasons. A scattering speed of the spark becomes higher in accordance that the peripheral speed of the grind stone of the grinder 101 becomes higher. In the case that the scattering speed of the spark is high, a plurality of spark regions tend to overlap in the imaged picture if the exposure time is long. Then, a plurality of streamline spark regions overlap, whereby the bursting spark region having three or more end portions is formed. FIG. 4 is a graph showing an exposure time of the imaging device 2, a rate of the numbers of the various spark regions with respect to the total of numbers of the various spark regions appearing in the imaged picture 6, in the case that the peripheral speed of the grind stone of the grinder 101 is 30 mm/sec. In this case, an interference spark region shown in FIG. 4 is a spark region formed by overlapping a plurality of spark regions (between the bursting spark regions, between the streamline spark regions, or between the bursting spark region and the streamline spark region). The rate of the number of the bursting spark regions with respect to the total of the various spark regions shown in FIG. 4 is a rate of the number of the bursting spark regions in which the interference spark region is not formed, with respect to the total of the various spark regions. The rate of the number of the streamline spark regions with respect to the total of the various spark regions shown in FIG. 4 is a rate of the number of the streamline spark regions in which the interference spark region is not formed, with respect to the total of the number of the various spark regions. As shown in FIG. 4, if the exposure time becomes longer, the number of the interference spark regions is increased, and the streamline spark regions are overlapped, whereby the bursting spark region is formed on a large scale. On the other hand, it is hard to seize a moment of the spark bursting by the imaging device 2 in accordance that the exposure time is made shorter, and a risk that the bursting spark appears as the streamline spark region having only two end portions on the imaged picture is increased. Accordingly, since there is a small risk that the interference spark region is formed, in the case that the peripheral speed of the grind stone of the grinder 101 is low, the exposure time of the imaging device 2 is made longer, and it is preferable to make the exposure time shorter in accordance that the peripheral speed of the grind stone of the grinder 101 is higher. In this case, in the present embodiment, the exposure time is set $\frac{1}{250}$ second. Further, the imaging device 2 carries out the imaging at intervals of $\frac{1}{200}$ second.

The detecting part 3 detects the spark region and the bursting spark region from each of the imaged pictures 6 which the imaging device 2 images. The detecting part 3 executes a first detecting step of detecting a spark candidate pixel group constructed by the pixels which are continuous along the pixel line X among M number of the pixel lines constructing each of the imaged pictures 6 and which have gray levels that are equal to or more than a first threshold value TH1.

The first detecting step is carried out as follows. First of all, as shown in FIG. 3, the detecting part 3 determines whether or not the gray level is equal to or more than the first threshold value TH1, alphabetically from the pixel X1 constructing one end portion of the pixel line X, with regard to the pixels constructing the pixel line X. In the present embodiment, the first threshold value TH1 is set to a value which is equal to or less than the gray level values of all the pixels constructing the spark regions 71 to 73, and all the pixels constructing the peripheral regions 71' to 73', and goes beyond the gray level values of all the pixels constructing the other region 70. As a method of setting the first threshold value TH1 to the value mentioned above, for example, there can be listed up a method of setting the gray level value indicating the gray level which slightly exceeds the gray level of the pixel having the maximum gray level to the first threshold value TH1, in the imaged picture 6 which an operator images by means of the imaging device 2 at a time when the spark is not generated.

The pixels (except a pixel Xa) from a pixel X1 to the pixel Xa constructing one end portion (This is an end portion in a side in which a pixel exists. Whether or not the gray level of the pixel X1 is equal to or more than the first threshold value TH1 is first determined.) of the peripheral region 71' are all pixels which construct the other region 70. Accordingly, the detecting part 3 determines that the gray level is less than the first threshold value TH1, with regard to the pixels (except the pixel Xa) from the pixel X1 to the pixel Xa. On the other hand, since the gray level of the pixel Xa constructing the peripheral region 71' is equal to or more than the first threshold value TH1, the detecting part 3 determines that the gray level of the pixel Xa is equal to or more than the first threshold value TH1. If it is determined that the gray level is equal to or more than the first threshold value TH1, the detecting part 3 has a look at the gray level of each of the pixels in the other side of the pixel line X, and detects a pixel Xc (constructing the other end portion of the peripheral region 71') one before the pixel in which the gray level is first less than the first threshold value TH1. Further, the detecting part 3 detects the pixel group constructed from all the pixels (including the pixel Xa and the pixel Xc) from the pixel Xa to the pixel Xc as a spark candidate pixel group 81.

When the detecting part 3 detects the spark candidate pixel group 81, it determines whether or not the gray level is equal to or more than the first threshold value TH1, with regard to the pixels in the other side of the pixel line X than the pixel Xc, and carries out the detection of the spark candidate pixel group. In the pixel line X, there are pixels constructing the spark regions 72 and 73, and the peripheral regions 72' and 73', and the gray levels of these pixels are equal to or more than the first threshold value TH1. Accordingly, the detecting part 3 detects all the pixels (including a pixel Xd and a pixel Xe) from the pixel Xd constructing one end portion of the peripheral region 72' to the pixel Xe constructing the other end portion of the peripheral region 72' as a spark candidate pixel group 82, and detects all the pixels (including a pixel Xf and a pixel Xg) from the pixel Xf constructing one end portion of the peripheral region 73' to the pixel Xg constructing the other end portion of the peripheral region 73' as a spark candidate pixel group 83.

The detecting part 3 executes a second detecting step with regard to each of the detected spark candidate pixel groups 81 to 83 after executing the first detecting step with regard to the pixel line X. In the second detecting step executed with regard to the spark candidate pixel group 81, the detecting part 3 detects a maximum gray level Cmax of the pixel which constructs the spark candidate pixel group 81 and has the maximum gray level, as shown in FIG. 3. Next, the detecting part 3 calculates a second threshold value TH2 corresponding to a threshold value which is less than the maximum gray level Cmax and is more than the first threshold value TH1, and having a predetermined rate with respect to the maximum gray level Cmax. The detecting part 3 binarizes the pixel constructing the spark candidate pixel group 81 by the calculated second threshold value TH2. Further, the detecting part 3 detects the pixel group constructed by the pixels in which the gray levels are equal to or more than the second threshold value TH2 as a spark pixel group 91, among the pixels constructing the spark candidate pixel group 81. In the same manner, the detecting part 3 executes the second detecting step with regard to the spark candidate pixel groups 82 and 83, and detects the spark pixel groups 92 and 93.

As mentioned above, the second detecting step is carried out per the spark candidate pixel group, and the second threshold value TH2 used in the second detecting step is less than the maximum gray level of the pixel constructing each of the spark candidate pixel groups, and has the predetermined rate with respect to the maximum gray level. As shown in FIG. 3, the gray level is larger in the spark regions 71 to 73 in comparison with the peripheral regions 71' to 73'. Accordingly, in each of the spark candidate pixel groups 81 to 83, it is possible to make the gray levels of the pixels constructing the peripheral regions 71' to 73' less than the second threshold value TH2. Therefore, it is possible to detect the spark pixel group constructed by the pixels constructing the spark region by executing the second detecting step.

The detecting part 3 prepares a binary image expressing the spark pixel group per imaged picture, by executing the first detecting step and the second detecting step mentioned above with regard to all the pixel lines constructing each of the imaged pictures. Subsequently, the detecting part 3 applies a thinning process to the binarized image of each of the imaged pictures. It is easy to accurately identify the end portion of the spark pixel group appearing in the binarized image, by applying the thinning process.

Figure 5:
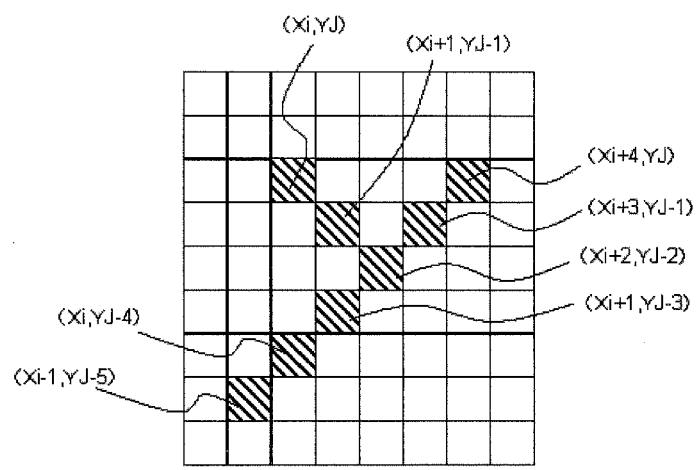
FIG. 5 is a view showing a part of a binarized image to which the thinning process is applied.

The detecting part 3 detects the spark region and the bursting spark region from the binarized image of each of the imaged pictures to which the thinning process is applied. The detection of the spark region first searches the pixel constructing the spark pixel group with regard to the binarized image to which the thinning process is applied. FIG. 5 is a view showing a part of the binarized image to which the thinning process is applied. In this case, in FIG. 5, it is assumed that a shaded pixel is a pixel which is determined as the pixel constructing the spark pixel group by the detecting part 3. As shown in FIG. 5, when the detecting part 3 detects a pixel (Xi, Yj) constructing the spark pixel group, it determines whether or not each of eight pixels around the pixel (Xi, Yj) is the pixel constructing the spark pixel group. As shown in FIG. 5, the detecting part 3 determines that a pixel (Xi+1, Yj−1) in eight peripheral pixels is the pixel constructing the spark pixel group. When the detecting part 3 determines whether or not each of eight peripheral pixels is the pixel constructing the spark pixel group, the detecting part 3 determines whether or not each of eight peripheral pixels of the pixel (Xi+1, Yj−1) which is determined to construct the spark pixel group in eight peripheral pixels is the pixels constructing the spark pixel group. As mentioned above, with regard to a pixel (Xi+2, Yj−2), a pixel (Xi+3, Yj−1), a pixel (Xi+4, Yj), a pixel (Xi+1, Yj−3), a pixel (Xi, Yj−4) and a pixel (Xi−1, Yj−5) which are determined as the pixel constructing the spark pixel group, the detecting part 3 determines whether or not it is the pixel constructing the spark pixel group, with regard to eight peripheral pixels of each of the pixels.

In this case, in a pixel (Xi, Yj), a pixel (Xi+4, Yj), and a pixel (Xi−1, Yj−5), only one pixel in eight peripheral pixels is determined as the pixel constructing the spark pixel group. The detecting part 3 identifies the pixel which is determined as the pixel in which only one pixel constructs the spark pixel group as the end portion pixel.

The detecting part 3 identifies the region constructed by the pixels (the pixel (Xi, Yj), the pixel (Xi+1, Yj−1), the pixel (Xi+2, Yj−2), the pixel (Xi+3, Yj−3), the pixel (Xi+4, Yj), the pixel (Xi+1, Yj−3), the pixel (Xi, Yj−4), and the pixel (Xi−1, Yj−5)) constructing the spark pixel groups which succeed a parallel direction (a lateral direction in FIG. 5) to the pixel line, an orthogonal direction, or a direction forming 45 degrees with respect to the pixel line, as the spark region.

When the detecting part 3 identifies the spark region, it determines whether or not the other pixels of the binarized image are the pixel constructing the spark pixel group, and finishes the detection of the spark region from the binarized image after determining with regard to all the pixels of the binarized image whether they are the pixel constructing the spark pixel group.

The detecting part 3 identifies each of the spark region having three or more pixels which are identified as the end portion pixel as the bursting spark region, among identified spark regions.

In this case, since the interference spark region has three or more end portion pixels, the detecting part 3 identifies the interference spark as the bursting region. Accordingly, in order to prevent the interference spark region from being generated, it is preferable to set the exposure time of the imaging device 2 to a shorter time in accordance that the peripheral speed of the grind stone of the grinder 101 becomes higher, as mentioned above.

The calculating part 4 calculates a total α of the spark region and a total β of the bursting spark region by summing up the numbers of the spark regions and the bursting spark regions with regard to the binarized image of each of the imaged picture which is identified (detected) by the detecting part 3 and is thinning processed, in each of all the imaged pictures, and calculates a rate (that is, a bursting rate) of the total β of the bursting spark region with respect to the total α of the spark region.

The calculating part 4 calculates a bursting rate Z in accordance with the following expression (1).

[Numerical Expression 1]

$$Z = \frac{\sum_{i=1}^{L} B}{\sum_{i=1}^{L} A} \quad (1)$$

Figure 6:
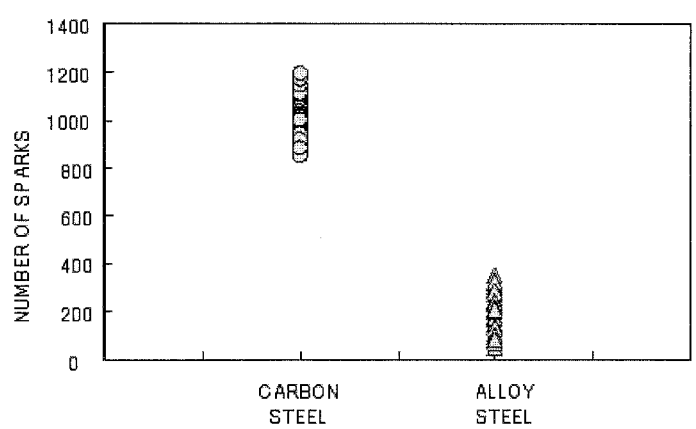
FIG. 6 is a graph showing the numbers of a spark generated during rubbing alloy steel, and a spark generated during rubbing carbon steel.

A: number of spark regions which are identified in binarized image of each of imaged pictures to which thinning process is applied B: number of bursting spark regions which are identified in binarized image of each of imaged pictures to which thinning process is applied L: number of imaged pictures In the case that the total α of the spark region is less than a third threshold value, the determining part 5 determines that the steel product 102 consists of alloy steel, and determines that the steel product 102 consists of carbon steel in the case that it is equal to or more than the third threshold value. It is possible to determine based on the total α of the spark regions whether the steel product consists of the alloy steel or the carbon steel, because the number of the sparks generated during rubbing by the grinder or the like is significantly small in the steel product consisting of alloy steel, in comparison with the steel product consisting of carbon steel. In this case, FIG. 6 shows the number of the sparks generated during rubbing quantity of the steel product consisting of alloy steel which include Cr and Mo and have different contents of Cr by the grinder, and the number of the sparks generated during rubbing quantity of the steel product consisting of carbon steel in which the carbon content is 0.1%, 0.2%, 0.27%, 0.33% and 0.44%. In this case, alloy steel means a steel that satisfies at least one of the following conditions 1 to 4.

Condition 1: content of Cr is equal to or more than 0.5%.
Condition 2: content of Ni is equal to or more than 0.5%.
Condition 3: content of Mo is equal to or more than 0.25%.
Condition 4: content of Cu is equal to or more than 0.25%.

Further, carbon steel means a steel that satisfies none of the conditions 1 to 4.

When the determining part 5 determines the steel product 102 consists of carbon steel, it determines based on the bursting rate Z the carbon content of the steel product 102. In this case, the determining part may determine the carbon percentage content itself or may determine a kind of the steel product 102 (a composition of the steel product) based on the determined carbon content. Further, results of determination may be displayed on a result display unit 51 such as a monitor, or may be stored in a storage unit 52 such as a hard disk, a memory.

Figure 7:
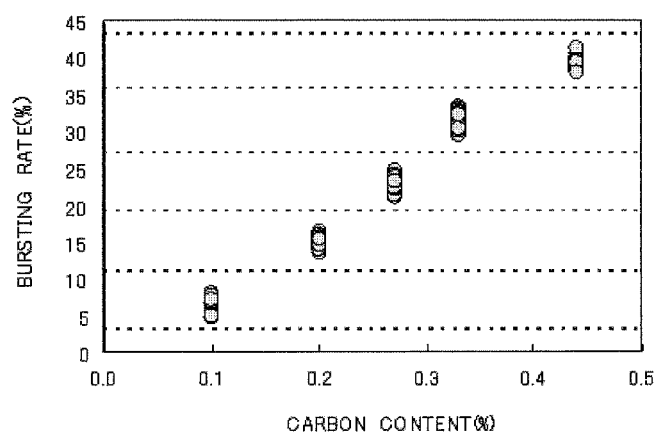
FIG. 7 is a graph showing a relation between a carbon content of a steel product and a bursting rate.

As mentioned above, in the material determining apparatus 1 in accordance with the present embodiment, the carbon content of the steel product 102 is determined based on the bursting rate Z corresponding to the rate of the total β of the bursting spark region with respect to the total α of the spark region. The actual bursting rate corresponding to the rate of the number of the bursting sparks with respect to the number of the sparks generated during rubbing the steel product 102 (that is, (number of bursting sparks)+(number of streamline sparks)) depends on the carbon content of the steel product 102, as shown in FIG. 7, but does not depend on the pressing force of the grinder 101 with respect to the steel product 102, the contact area between the steel product 102 and the grinder 101, and the like. Accordingly, since the result of determination of the material determining apparatus 1 is not affected by the pressing force of the grinder 101 with respect to the steel product 102, the contact area between the steel product 102 and the grinder 101, and the like, the material determining apparatus 1 can stably and precisely determine the carbon content of the steel product 102. Further, as shown in FIG. 7, the bursting rate Z is different at about 10% per 0.1% difference of the carbon content, between 0.1 and 0.5% of the carbon content. Accordingly, the material determining apparatus 1 can precisely determine the carbon content by 0.1% unit between 0.1 and 0.5% of the carbon content.

The executing method of the first detecting step carried out by the detecting part 3 is not limited to the method mentioned above. For example, the first detecting step can be executed as follows.

First of all, the detecting part 3 determines whether or not the gray level is equal to or more than the first threshold value TH1 alphabetically from the pixel X1 constructing one end portion of the pixel line X, with regard to the pixels constructing one pixel line (which is assumed as the pixel line X shown in FIG. 2 in this case) constructing each of the imaged pictures 6 imaged by the imaging device 2. As shown in FIG. 3, if the detecting part 3 detects that the gray level of the pixel Xa is equal to or more than the first threshold value TH1, it detects the pixel Xa determined to be equal to or more than the first threshold TH1 and, the pixel group constructed by the pixels between the pixel Xa and the pixel X(a+k) which is a predetermined pixel number K away from the pixel Xa to the other side of the pixel line X (that is, the pixel group constructed by the pixels Xa to X(a+k−1)) as the spark candidate pixel group 81. The detecting part 3 determines whether or not the gray level is equal to or more than the first threshold value TH1, with regard to the pixels existing in the other side of the pixel line X from the spark candidate pixel group 81, and detects the spark candidate pixel group.

In the method mentioned above, it is possible to prevent the pixels constructing the spark region 71 and the pixels constructing the spark region 72 from being included in the pixels constructing one spark candidate pixel group 81, for example, as shown in FIG. 3, by setting the predetermined pixel number K to the pixel number corresponding to a dimension in the direction of the pixel line X of the spark region or a dimension which is slightly larger than the dimension. If the pixels constructing the spark region 71 and the pixels constructing the spark region 72 are included in the pixels constructing one spark candidate pixel group 81, the second threshold value comes to a value having a predetermined rate with respect to the maximum gray level Cmax of the spark region 71 having the large gray level. Accordingly, there is a possibility that the pixels constructing the spark region 72 become less than the second threshold value TH2. Therefore, the pixels constructing the spark region 72 cannot construct the spark pixel group. Accordingly, all the pixels constructing the spark region can construct the spark pixel group by setting the predetermined pixel number K to the pixel number corresponding to the dimension in the direction of the pixel line X of the spark region or the dimension which is slightly larger than the dimension mentioned above, and all the pixels constructing the spark region can come to the pixels constructing the spark region detected by the detected part 3.

Figure 8:
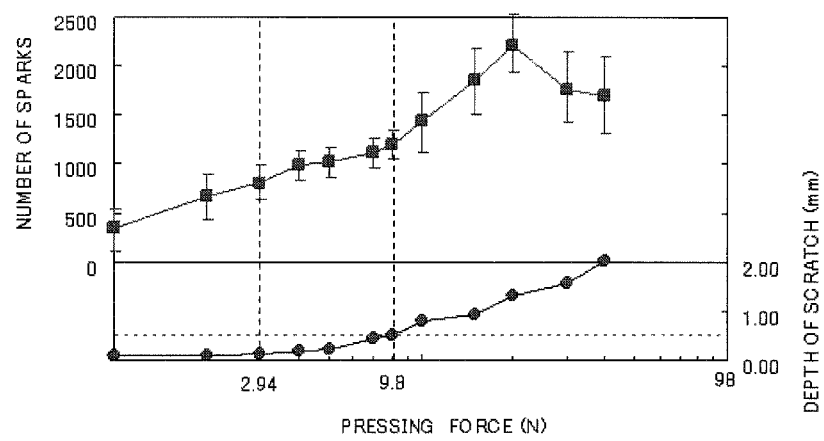
FIG. 8 is a graph showing a relation between a pressing force of a grinder applied to the steel product, and the number of the generated sparks and a depth of a scratch applied to the steel product.

Further, it is preferable that the pressing force of the grinder 101 applied to the steel product 102 is equal to or more than 2.94 N and equal to or less than 9.8 N. As shown in FIG. 8, if the pressing force is made equal to or more than 2.94 N, the number of the sparks generated during rubbing the steel product 102 by the grinder 101 is large, and it is possible to make a difference between the bursting rate Z and the actual bursting rate small. Accordingly, it is possible to precisely and stably determine the carbon content of the steel product 102.

Further, as shown in FIG. 8, if the pressing force is made equal to or less than 9.8 N, it is possible to determine the material of the steel product 102 by the material determining apparatus 1 in accordance with the present embodiment, without giving any deep scratch to the steel product 102.

Figure 9:
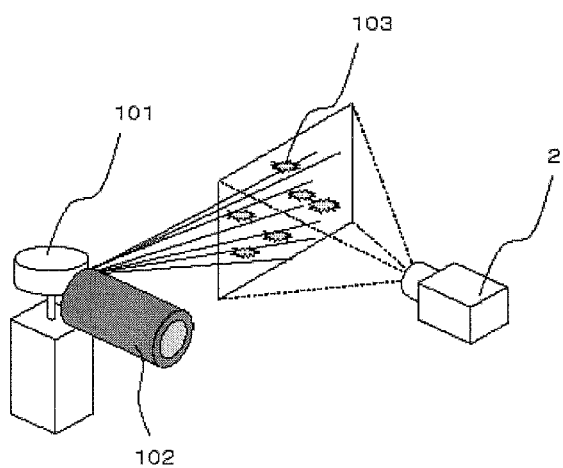
FIG. 9 is a schematic view showing a state in which the spark generated during rubbing a end face of the steel product by the grinder is imaged.

Further, in the case that the steel product 102 is formed into a cylindrical shape or a circular columnar shape, it is preferable to set the position rubbed by the grinder 101 in the steel product 102 to the end face in the end portion in the axial direction of the steel product 102 as shown in FIG. 9 in place of the peripheral surface of the steel product 102, because of the following reason. There is a case that a layer (so-called scale) having carbon content dispersion is formed in the peripheral surface of the steel product 102, and the result of determination is not stable. Further, there can be considered to rub the peripheral surface of the steel product 102 by removing the scale, however, there is a problem that a large scratch is generated in the steel product 102 if the scale is removed. Further, there is a case that oil or the like is applied to the peripheral surface of the steel product 102, and there is a problem that the oil is removed if the peripheral surface of the steel product 102 is rubbed.

The component constructing the material of the steel product 102 includes the alloy component constructed by the elements such as Cr, Mo, Ti, Mn and the like in addition to the carbon component. Accordingly, in the case of more precisely determining the material of the steel product 102, not only the carbon content of the steel product 102, but also the alloy component content of the steel product 102 comes to an important element. As mentioned above, the carbon content of the steel product 102 can be precisely determined based on the bursting rate Z. However, since the change in the bursting rate Z is small in comparison with the change in the alloy component content of the steel product 102, the alloy component content of the steel product 102 cannot be precisely determined based on the bursting rate Z. A description will be given below of a preferable structure for more precisely determining the material of the steel product 102 which is determined as the carbon steel as mentioned above. In the preferable structure mentioned above, the material determining apparatus 1 is provided with a fluorescent X-ray analyzing apparatus in addition to the imaging device 2, the detecting part 3, the calculating part 4, the determining part 5, the result display unit 51, and the storage unit 52. The fluorescent X-ray analyzing apparatus is an apparatus carrying out a fluorescent X-ray analysis with respect to the steel product 102. In this case, since the structure of the fluorescent X-ray analyzing apparatus is a known structure, a description of the fluorescent X-ray analyzing apparatus will not be given here. If the determining part 5 determines based on the bursting rate Z that the steel product 102 consists of the carbon steel as mentioned above, it determines the carbon content of the steel product 102 based on the bursting rate Z, and waits for an input of the result of analysis of the fluorescent X-ray analysis of the steel product 102. In this case, if the fluorescent X-ray analysis is carried out by the fluorescent X-ray analyzing apparatus with respect to the steel product 102 which is determined as the carbon steel by the determining part 5, and the result of analysis is input to the determining part 5 from the fluorescent X-ray analyzing apparatus, the determining part 5 determines the alloy component content of the steel product 102 based on the input result of analysis. Further, the determining part 5 determines the material of the steel product 102 based on the alloy component content and the carbon content. In accordance with the method of determining the alloy component content of the steel product 102 from the result of analysis of the fluorescent X-ray analysis, it is possible to more precisely determine the alloy component content of the steel product 102 than the case of determining the alloy component content of the steel product 102 based on the bursting rate Z. Therefore, in accordance with the preferable structure mentioned above, it is possible to more precisely determine the material of the steel product 102.

Further, even in the case that the carbon content is not determined with regard to the steel product 102 which is determined as alloy steel, like the present embodiment, the determining part 5 may determine the material of the steel product 102 which is determined to be the alloy steel, in accordance with the following manner. If the determining part 5 determines based on the bursting rate Z that the steel product 102 consists of the alloy steel as mentioned above, it waits for the input of the result of analysis of the fluorescent X-ray analysis with respect to the steel product 102 without determining the carbon content. It the fluorescent X-ray analysis is carried out with respect to the steel product 102, and the result of analysis is input, the determining part 5 determines the alloy component content of the steel product 102 based on the input result of analysis. Further, the determining part 5 determines the material of the steel product 102 based on the determined alloy component content.

What is claimed is:

1. A material determining apparatus for a steel product comprising:
    an imaging device for continuously imaging a spark generated during rubbing the steel product at a plurality of times;
    a detecting part for detecting spark regions and bursting spark regions having three or more end portions among the spark regions, from each of the imaged pictures imaged by the imaging device;
    a calculating part for calculating a total of the spark regions and a total of the bursting spark regions by summing up the numbers of the spark regions and the bursting spark regions detected by the detecting part with regard to each of all the imaged pictures, so as to calculate a rate of the total of the bursting spark regions with respect to the total of the spark regions; and
    a determining part for determining a carbon content of the steel product based on the rate, wherein
    the detecting part carries out the following steps:
    a first detecting step of detecting a spark candidate pixel group constructed by pixels which are continuous along one pixel line among pixel lines constructing each of the imaged pictures imaged by the imaging device, and which have gray levels that are equal to or more than a first threshold value;
    a second detecting step of detecting a maximum gray level among the gray levels of the pixels constructing the spark candidate pixel group, and binarizing the pixels constructing the spark candidate pixel group by a second threshold value which is less than the maximum gray level and is more than the first threshold value, and which has a predetermined rate with respect to the maximum gray level, thereby detecting the pixels constructing a spark pixel group from the pixels constructing the spark candidate pixel group; and
    an identifying step of preparing a binarized image expressing the spark pixel group for each of the imaged pictures by executing the first detecting step and the second detecting step with respect to all the pixel lines constructing each of the imaged pictures, and identifying the spark pixel groups which are continuous with any direction in the each of the binarized images as the spark region.

2. The material determining apparatus for a steel product as claimed in claim 1, wherein the detecting part applies a thinning process to the binarized images, identifies the spark pixel groups which are continuous with any direction in the each of the binarized images applied to the thinning process as the spark region, and identifies the spark region as the bursting spark region if the spark region has three or more end portions.

3. The material determining apparatus for a steel product as claimed in claim 1, wherein the steel product consists of carbon steel or alloy steel, and wherein the determining part determines that the steel product consists of alloy steel in the case that the total of the spark regions is less than a third threshold value, determines that the steel product consists of carbon steel in the case that it is equal to or more than the third threshold value, and determines the carbon content of the steel product based on the rate in the case of determining that the steel product consists of the carbon steel.

4. The material determining apparatus for a steel product as claimed in claim 1, wherein the determining part determines the material of the steel product based on the carbon content determined based on the rate, and an alloy component content of the steel product determined by a method which does not utilize a spark generated during rubbing the steel product.

5. A material determining method for a steel product comprising:
    an imaging step of continuously imaging a spark generated during rubbing the steel product at a plurality of times by using an imaging device;
    a detecting step of detecting spark regions and bursting spark regions having three or more end portions among the spark regions, by performing image processing to each of the imaged pictures imaged by the imaging device in the imaging step;
    a calculating step of calculating a total of the spark regions and a total of the bursting spark regions by summing up the numbers of the spark regions and the bursting spark regions detected in the detecting step with regard to each of all the imaged pictures, so as to calculate a rate of the total of the bursting spark regions with respect to the total of the spark regions; and
    a determining step of determining a carbon content of the steel product based on the rate, wherein
    the detecting step includes:
    a first detecting step of detecting a spark candidate pixel group constructed by pixels which are continuous along one pixel line among pixel lines constructing each of the imaged pictures imaged by the imaging step, and which have gray levels that are equal to or more than a first threshold value;
    a second detecting step of detecting a maximum gray level among the gray levels of the pixels constructing the spark candidate pixel group, and binarizing the pixels constructing the spark candidate pixel group by a second threshold value which is less than the maximum gray level and is more than the first threshold value, and which has a predetermined rate with respect to the maximum gray level, thereby detecting the pixels constructing a spark pixel group from the pixels constructing the spark candidate pixel group; and
    an identifying step of preparing a binarized image expressing the spark pixel group for each of the imaged pictures by executing the first detecting step and the second detecting step with respect to all the pixel lines constructing each of the imaged pictures, and identifying the spark pixel groups which are continuous with any direction in the each of the binarized images as the spark region.

6. The material determining method for a steel product as claimed in claim 5, wherein the imaging step images the spark generated by rubbing the steel product by the rubbing member, in a state in which the rubbing member is pressed to the steel product by a force which is equal to or more than 2.94 N and equal to or less than 9.8 N.

\* \* \* \* \*